(12) United States Patent
Song et al.

(10) Patent No.: US 9,506,857 B2
(45) Date of Patent: Nov. 29, 2016

(54) AUTOMATIC OBSERVATION APPARATUS FOR DETECTING MINERAL SAMPLES

(71) Applicant: CHINA UNIVERSITY OF PETROLEUM (EAST CHINA), Qingdao, Shandong (CN)

(72) Inventors: Ying Song, Qingdao (CN); Yongqiang Yang, Qingdao (CN); Longwei Qiu, Qingdao (CN); Yuming Zhao, Qingdao (CN); Weichao Yang, Qingdao (CN); Ying Qi, Qingdao (CN); Andrei Stepashko, Khabarovsk (RU)

(73) Assignee: CHINA UNIVERSITY OF PETROLEUM (EAST CHINA), Qingdao (CN)

( * ) Notice: Subject to any disclaimer, the term of this patent is extended or adjusted under 35 U.S.C. 154(b) by 0 days.

(21) Appl. No.: 14/909,732

(22) PCT Filed: Jun. 16, 2015

(86) PCT No.: PCT/CN2015/081561
§ 371 (c)(1),
(2) Date: Feb. 2, 2016

(87) PCT Pub. No.: WO2015/192767
PCT Pub. Date: Dec. 23, 2015

(65) Prior Publication Data
US 2016/0187255 A1    Jun. 30, 2016

(30) Foreign Application Priority Data

Jun. 19, 2014   (CN) .......................... 2014 1 0275785

(51) Int. Cl.
*B23P 19/08*         (2006.01)
*G01N 21/41*        (2006.01)
(Continued)

(52) U.S. Cl.
CPC .......... *G01N 21/4133* (2013.01); *G01N 21/87* (2013.01); *G01N 33/38* (2013.01); *G01N 2201/025* (2013.01)

(58) Field of Classification Search
CPC ....... B23P 19/04; B23P 19/048; B23P 19/10; B23Q 3/00; B23Q 3/06; B23Q 3/061; B23Q 3/186; B23Q 11/0064; B23Q 17/006; B25B 11/02
See application file for complete search history.

(56) References Cited

U.S. PATENT DOCUMENTS

| 4,188,116 A * | 2/1980 | Bartfay-Szabo ....... G01N 21/43 356/137 |
| 6,870,606 B2 | 3/2005 | Klingler |

(Continued)

FOREIGN PATENT DOCUMENTS

| CN | 2342380 Y | 10/1999 |
| CN | 2662238 Y | 12/2004 |

(Continued)

OTHER PUBLICATIONS

Huang, Zuoliang "Crystal Optics Interpretation of Gem Refractometer Measuring Refractive Index" Journal of Tianjin University of Commerce Year 2004, Issue 3, p. 36-40.

*Primary Examiner* — Lee D Wilson
(74) *Attorney, Agent, or Firm* — Maschoff Brennan

(57) ABSTRACT

An automatic observation apparatus for detecting mineral samples comprises a base (1), a supporting arm (2), a sample fixing device (3), a stepper motor (4), a high-definition camera (5) and a control system (6). A refractometer is fixed on the base (1). A vertical through hole is formed at the top end of the supporting arm (2), and a lifting rod (211) penetrates through the vertical through hole and is matched with the vertical through hole in shape. A cavity is formed at the top end of the supporting arm (2), a gear (216) is mounted in the cavity, and the gear (216) is meshed with a rack (215) of the lifting rod (211). The sample fixing device (3) is a right-hexagonal-prism shell with the top end sealed, a spring (312) is arranged in a vertical hole of the sample fixing device, a sample locating head fixing device (314) is arranged at the lower end of the spring (312), a blind hole is formed in the lower end of the sample locating head fixing device (314), and a sample locating head (316) is matched with the blind hole in the lower end of the sample locating head fixing device (314). The apparatus can conveniently and efficiently fix samples, stray light interference is avoided, mineral samples can be rotated to be observed from different angles, and mineral sample detection accuracy is improved.

6 Claims, 3 Drawing Sheets

(51) Int. Cl.
*G01N 21/87* (2006.01)
*G01N 33/38* (2006.01)

(56) References Cited

U.S. PATENT DOCUMENTS

| | | | | |
|---|---|---|---|---|
| 2010/0281667 | A1* | 11/2010 | Aisaki | F16H 59/105 29/281.1 |
| 2014/0373327 | A1* | 12/2014 | Wang | B30B 1/38 29/252 |
| 2015/0260132 | A1* | 9/2015 | Oliver | F02M 37/0011 29/428 |
| 2016/0038596 | A1* | 2/2016 | Wright | A61K 9/0019 604/69 |
| 2016/0068209 | A1* | 3/2016 | Sakamoto | B25B 11/02 29/281.1 |
| 2016/0187255 | A1* | 6/2016 | Song | G01N 21/87 356/128 |

FOREIGN PATENT DOCUMENTS

| | | |
|---|---|---|
| CN | 2676191 Y | 2/2005 |
| CN | 202452955 U | 9/2012 |
| CN | 104007070 A | 8/2014 |
| EP | 1955055 B1 | 8/2009 |

* cited by examiner

US 9,506,857 B2

AUTOMATIC OBSERVATION APPARATUS FOR DETECTING MINERAL SAMPLES

TECHNICAL FIELD

The present invention belongs to the field of experimental detection, and particularly relates to an automatic observation apparatus for detecting mineral samples, which is used for realizing the fixation, automatic rotation and automatic observation of mineral samples.

BACKGROUND OF THE INVENTION

At present, the known ways of observing and identifying mineral samples by some optical instruments are almost all to place samples on an optical surface coated with refracting oil, fix and rotate the mineral samples by hands, and then observe directly from the eyepiece window by eyes to obtain readings at different angles of rotation of the samples. Such ways not only are complex in operation and low in efficiency and highly depend upon the proficiency and experience of the observers, but also fail to realize quantified rotation of samples. A too narrow eyepiece window also brings great inconvenience to the observation and identification, and the observed image can not be saved. Meanwhile, due to the unsealed sample observation environment, it is unable to avoid the stray light interference from the external environment during the rotation of samples by fingers, and also difficult to ensure close and stable contact between undetermined mineral samples to be detected and the optical surface so that the observers can not observe the accurate optical characteristics of the mineral samples to be detected from the optical instruments. Consequently, there are large errors in the obtained identification results of the minerals. When small mineral samples are fixed and rotated by hands, the fingers are likely to touch the virulent refracting oil so that the physical health of those who are identifying the samples is threatened; and the environment is polluted.

Utility Model Patent CN200420017243.8, titled "JEWEL FIXING AND ROTATING APPARATUS", discloses an apparatus for fixing and rotating jewels, where a left positioning slider guide rail and a right positioning slider guide rail are respectively provided on two sides of a main frame, a rotary dial central body is inserted into a center hole of the main frame, and a jewel positioning head fixing hole is provided at a jewel pressing rod shaft end of a jewel pressing rod. When in use, the apparatus is fixed on an optical instrument by adjusting the rotating and positioning screw stem handles at two ends first, then an external thread lifting bolt handle is rotated to adjust the up-down position of the jewel positioning head so that the jewel is compressed and fixed, and finally the jewel can be observed from various angles by rotating the rotary dial. This utility model highly depends upon the proficiency and experience of the detectors, fails to realize reliable fixation of the optical instrument and also accurate and automatic quantified rotation of samples, fails to avoid stray light interference in the contact surfaces and the eyepiece, and also fails to save the observed results.

SUMMARY OF THE INVENTION

To overcome deficiencies, such as low efficiency, large error, incapability of quantitatively and accurately observing optical characteristics of minerals, harmful to physical health of those who are identifying samples, and incapability of fixing the samples firmly by hands and avoiding stray light interference, of holding mineral samples by hands and observing directly from the eyepiece window in the prior art, the present invention provides an automatic observation apparatus for detecting mineral samples, where samples are fixed by mechanical apparatuses so that the samples are fixed conveniently and efficiently; furthermore, the samples are accurately positioned and rotated by controlling a stepper motor by a computer, and an image observed in the eyepiece is transmitted onto a computer screen by a camera and may be saved in a specified file. In this way, the working efficiency of detecting mineral samples and the accuracy of identification are both improved, and the requirements on the proficiency and experience of the mineral detectors are reduced.

To achieve the above purposes, the present invention employs the following technical solutions.

An automatic observation apparatus for detecting mineral samples is provided, including a base, a supporting arm, a sample fixing device, a stepper motor, a high-definition camera and a control system, characterized in that a refractometer is fixed on the base; the supporting arm is L-shaped, a vertical through hole is formed at the top end of the supporting arm, and a lifting rod penetrates through the vertical through hole and is matched with the vertical through hole in shape; the lifting rod is a cylinder having a frustum at the top end; a drive rack is provided on the side of the cylinder of the lifting rod, and a vertical through hole is formed in the lifting rod; a stepper motor is mounted at the top end of the frustum of the lifting rod, an output shaft of the stepper motor penetrates through the vertical through hole of the lifting rod to be connected with the sample fixing device, and the sample fixing device is in shaft-hole fit and interference connection with the output shaft of the stepper motor; a cavity is formed at the top end of the supporting arm, a gear is mounted in the cavity, and the gear is meshed with the rack of the lifting rod; a drive shaft horizontally penetrates through the center of the gear and is fixedly connected with the gear, a cross-section of the drive shaft is a regular hexagon, a left knob and a right knob are respectively provided at two ends of the drive shaft, and the lifting rod is positioned by a positioning pin placed at the upper end of the supporting arm; the sample fixing device is a regular hexagonal prism shell with the top end sealed, a spring is arranged in a vertical hole of the sample fixing device, a sample positioning head mounting device is arranged at the lower end of the spring, and the sample positioning head mounting device is clamped in the vertical hole of the sample fixing device by the pin to prevent it from falling off; a blind hole is formed at the lower end of the sample positioning head fixing device and has a regular hexagonal cross-section of the blind hole, the sample positioning head has a regular hexagonal cross-section and is matched with the blind hole at the lower end of the sample positioning head fixing device; the sample positioning head fixing device is magnetized, and the sample positioning head made of metal is sucked in the blind hole; a soft rubber cushion is stuck to the lower end of the sample positioning head; the high-definition camera is connected with a data card by a first transmission cable, and the data card is connected with the control system by a second transmission cable; and the stepper motor is connected with a stepper motor driver by a third transmission cable, the stepper motor driver is connected with a stepper motor driving card by a fourth transmission cable, and the stepper motor is connected with the control system by a fifth transmission cable.

Compared with the prior art, the present invention has the following beneficial effects: fixing mineral samples by mechanical apparatuses, the mineral samples are fixed conveniently and efficiently; sealing the observation environment by the mechanical apparatuses, the stray light interference is avoided; quantitatively rotating the samples by electromechanical control equipment, the mineral samples are observed at different angles of rotation; transmitting test results of mineral samples to be detected in digital signals, the accuracy of detection of mineral samples is improved.

DETAILED DESCRIPTION OF THE PREFERRED EMBODIMENTS

Figure 1:
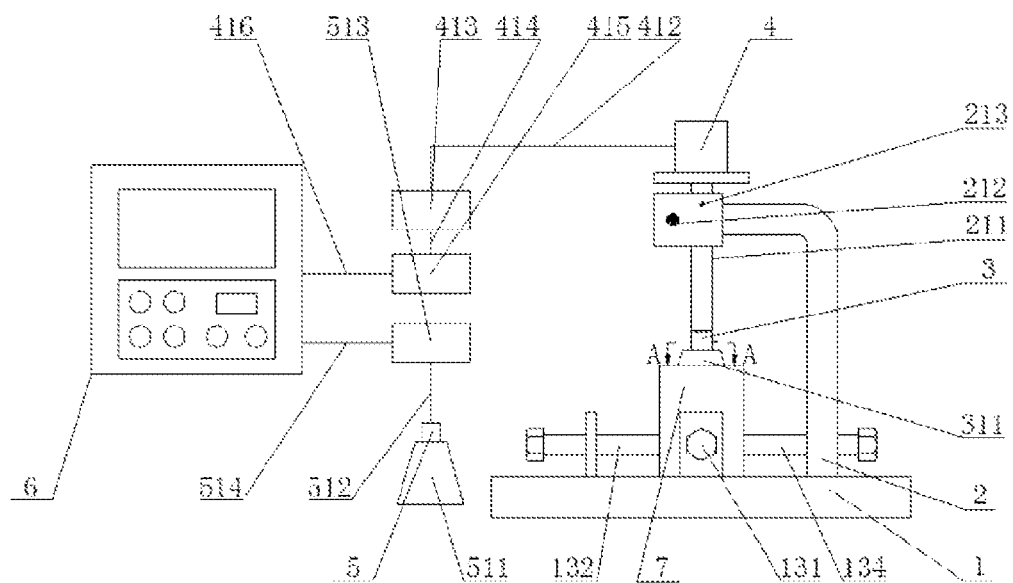
FIG. 1 is a front view of an automatic observation apparatus for detecting mineral samples.
Figure 2:
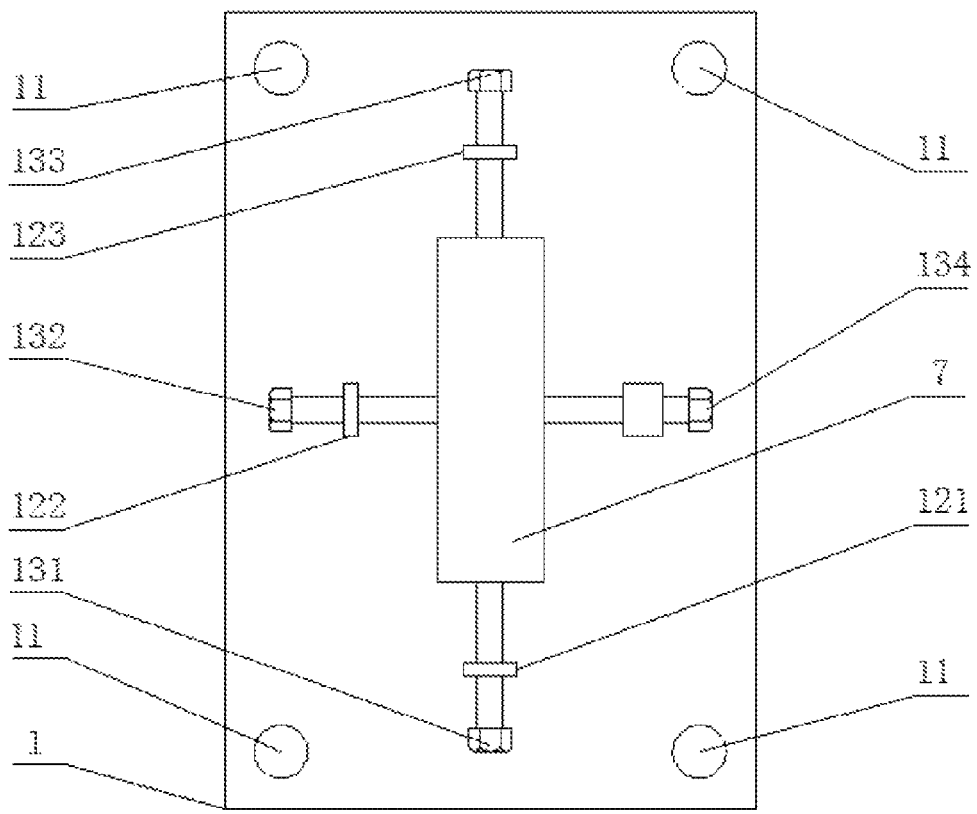
FIG. 2 is a top view of the automatic observation apparatus for detecting mineral samples.
Figure 3:
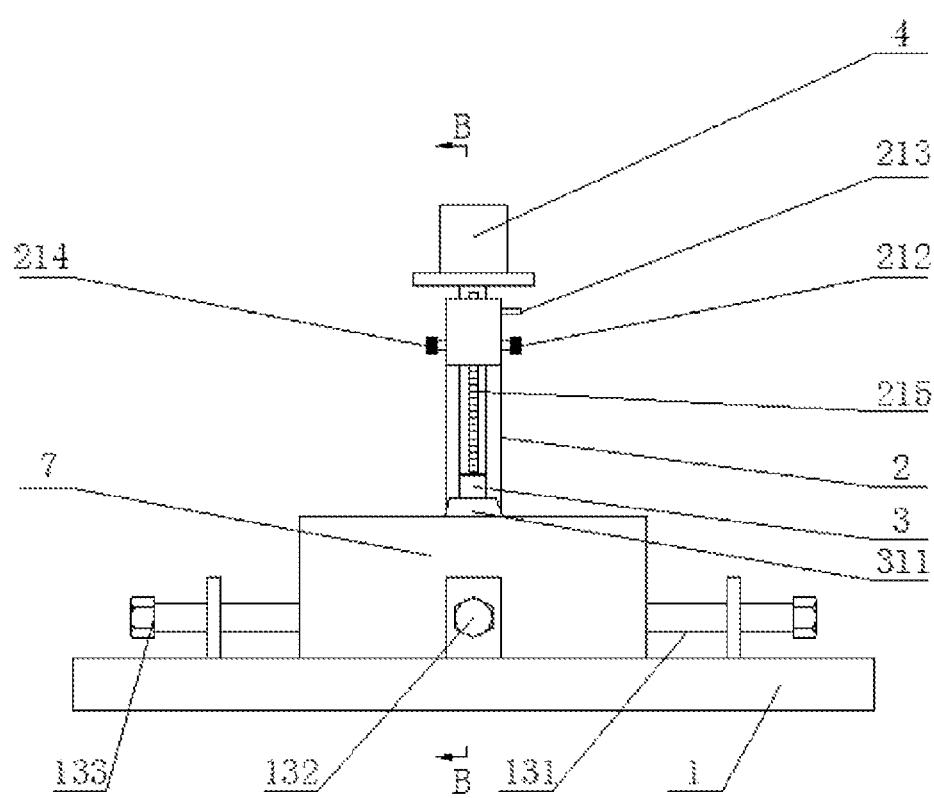
FIG. 3 is a left view of the automatic observation apparatus for detecting mineral samples.
Figure 4:
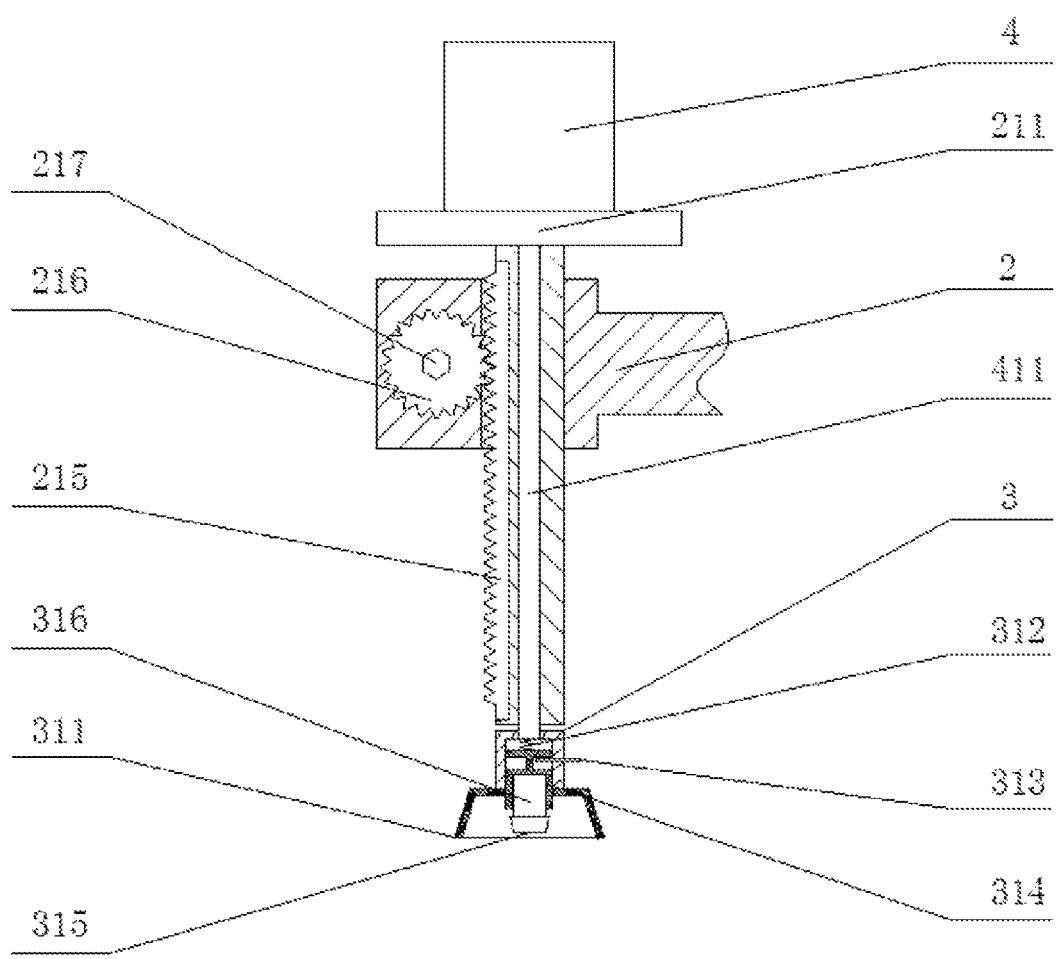
FIG. 4 is a sectional view of a lifting rod of the automatic observation apparatus for detecting mineral samples.

As shown in FIG. 1, an automatic observation apparatus for detecting mineral samples includes a base 1, a supporting arm 2, a sample fixing device 3, a stepper motor 4, a high-definition camera 5 and a control system 6.

The base 1 is a rectangular metal plate, a through hole 11 is respectively formed at four corners of the base 1, and the base 1 is fixed on a desktop by passing four screws through the through holes 11; a first lug 121, a second lug 122 and a third lug 123 are provided on the base 1, and the supporting arm 2 is embedded in the base 1; the first lug 121 is arranged in opposite to the third lug 123, the second lug 122 is arranged in opposite to the supporting arm 2, and a connecting line of the first lug 121 and the third lug 123 is vertical to a connecting line of the second lug 122 and the supporting arm 2; a threaded through hole is formed on the first lug 121, and a first screw 131 is mounted in the threaded through hole; a threaded through hole is formed on the second lug 122, and a second screw 132 is mounted in the threaded through hole; a threaded through hole is formed on the third lug 123, and a third screw 133 is mounted in the threaded through hole; a threaded through hole is formed at the lower end of the supporting arm 2, and a fourth screw 134 is mounted in the threaded through hole; the first screw 131, the second screw 132, the third screw 133 and the fourth screw 134 are in a same plane which is parallel to the base 1, and the first screw 131, the second screw 132, the third screw 133 and the fourth screw 134 can be screwed in or out in order to fix the refractometer.

The supporting arm 2 is L-shaped to support the lifting rod 211;

a vertical through hole is formed at the top end of the supporting arm 2, and a lifting rod 211 penetrates through the vertical through hole and is matched with the vertical through hole in shape;

the lifting rod 211 is a cylinder having a frustum at the top end; a drive rack 215 is provided on the side of the cylinder of the lifting rod 211, and a vertical through hole is formed in the lifting rod 211; a stepper motor 4 is mounted at the top end of the frustum of the lifting rod 211, an output shaft 411 of the stepper motor 4 penetrates through the vertical through hole of the lifting rod 211 to be connected with the sample fixing device 3, and the sample fixing device 3 is in shaft-hole fit and interference connection with the output shaft 411 of the stepper motor to prevent the relative motion between the sample fixing device 3 and the output shaft 411 of the stepper motor; and a cavity is formed at the top end of the supporting arm 2, a gear 216 is mounted in the cavity, and the gear 216 is meshed with the rack 215 of the lifting rod; a drive shaft 217 horizontally penetrates through the center of the gear 216 and is fixedly connected with the gear 216, a cross-section of the drive shaft 217 is a regular hexagon, a left knob 212 and a right knob 214 are respectively provided at two ends of the drive shaft 217, and the rotation of the left knob 212 and the right knob 214 can rotate the gear 216 to drive the lifting rod 211 to lift up and down so as to realize the up-down movement; and the lifting rod 211 is positioned by a positioning pin 213 placed at the upper end of the supporting arm 2.

The sample fixing device 3 is a regular hexagonal prism shell with the top end sealed, a spring 312 is arranged in a vertical hole of the sample fixing device 3, a sample positioning head mounting device 314 is arranged at the lower end of the spring 312, and the sample positioning head mounting device 314 is clamped in the vertical hole of the sample fixing device 3 by the pin 313 to prevent it from falling off;

a blind hole is formed at the lower end of the sample positioning head fixing device 314 and has a regular hexagonal cross-section of the blind hole, the sample positioning head 316 has a regular hexagonal cross-section and is matched with the blind hole at the lower end of the sample positioning head fixing device 314; the sample positioning head fixing device 314 is magnetized, and the sample positioning head 316 made of metal is sucked in the blind hole; a soft rubber cushion 315 is stuck to the lower end of the sample positioning head 316, and the soft rubber cushion 315 is used for directly contacting the samples to be detected for the purpose of fixing the samples.

A rubber cup 311 is provided outside the sample positioning head fixing device 314, and during the detection, the rubber cup 311 may shield light from the outside to form an enclosed space.

The rotational motion of the output shaft 411 of the stepper motor is transferred in turn through the sample fixing device 3 and the sample positioning head fixing device 314 to the sample positioning head 316, and the mineral samples to be detected is rotated by the sample positioning head 316.

The high-definition camera 5 is arranged in an enclosed hood 511, and when in use, the enclosed hood 511 is placed at the eyepiece window of the refractometer, and then the high-definition camera 5 may read a picture at the eyepiece window of the refractometer in real time.

The high-definition camera 5 is connected with a data card 513 by a first transmission cable 512, and the data card 513 is connected with the control system 6 by a second transmission cable 514; after the high-definition camera 5 reads a picture at the eyepiece window of the refractometer, the observed information is transferred to the data card 513 by the first transmission cable 512, and the information is then transmitted to the control system 6 by the second transmission cable 514 from the data card 513; and the control system 6 may observe an image in the eyepiece, and also may store and output the observed image to a specified file.

The stepper motor 4 is connected with a stepper motor driver 413 by a third transmission cable 412, the stepper motor driver 413 is connected with a stepper motor driving card 415 by a fourth transmission cable 414, and the stepper motor driving card 415 is connected with the control system 6 by a fifth transmission cable 416.

The control system 6 sends a stepper motor driving signal which is transmitted to the stepper motor driving card 415 by the transmission cable 416, the stepper motor driving card 415 converts the driving signal into a driving pulse which is transmitted to the stepper motor driver 413 by the transmission cable 414, and the stepper motor driver 413 sends a stepper motor driving signal which is transmitted to the stepper motor 4 by the transmission cable 412 to complete the driving of the stepper motor 4.

The control system 6 controls the rotational motion of the stepper motor 4, and the control system 6 can realize a rotation of 90°, 180° and 360° or continuous rotation of the stepper motor; and the angle of rotation of the mineral samples to be detected is directly determined by the angle of rotation of the stepper motor 4. When the stepper motor 4 is in a continuous rotation operating mode, the control system 6 can input a specified angle to which the stepper motor 4 rotates, and the control system 6 can automatically save an image and input the image into a specified file.

What is claimed is:

1. An automatic observation apparatus for detecting mineral samples, comprising a base, a supporting arm, a sample fixing device, a stepper motor, a high-definition camera and a control system, characterized in that a refractometer is fixed on the base; the supporting arm is L-shaped, a vertical through hole is formed at the top end of the supporting arm, and a lifting rod penetrates through the vertical through hole and is matched with the vertical through hole in shape; the lifting rod is a cylinder having a frustum at the top end; a drive rack is provided on the side of the cylinder of the lifting rod, and a vertical through hole is formed in the lifting rod; a stepper motor is mounted at the top end of the frustum of the lifting rod, an output shaft of the stepper motor penetrates through the vertical through hole of the lifting rod to be connected with the sample fixing device, and the sample fixing device is in shaft-hole fit and interference connection with the output shaft of the stepper motor; a cavity is formed at the top end of the supporting arm, a gear is mounted in the cavity, and the gear is meshed with the rack of the lifting rod; a drive shaft horizontally penetrates through the center of the gear and is fixedly connected with the gear, a cross-section of the drive shaft is a regular hexagon, a left knob and a right knob are respectively provided at two ends of the drive shaft, and the lifting rod is positioned by a positioning pin placed at the upper end of the supporting arm; the sample fixing device is a regular hexagonal prism shell with the top end sealed, a spring is arranged in a vertical hole of the sample fixing device, a sample positioning head mounting device is arranged at the lower end of the spring, and the sample positioning head mounting device is clamped in the vertical hole of the sample fixing device by the pin to prevent it from falling off; a blind hole is formed at the lower end of the sample positioning head fixing device and has a regular hexagonal cross-section of the blind hole, the sample positioning head has a regular hexagonal cross-section and is matched with the blind hole at the lower end of the sample positioning head fixing device; the sample positioning head fixing device is magnetized, and the sample positioning head made of metal is sucked in the blind hole; a soft rubber cushion is stuck to the lower end of the sample positioning head; the high-definition camera is connected with a data card by a first transmission cable, and the data card is connected with the control system by a second transmission cable; and the stepper motor is connected with a stepper motor driver by a third transmission cable, the stepper motor driver is connected with a stepper motor driving card by a fourth transmission cable, and the stepper motor is connected with the control system by a fifth transmission cable.

2. The automatic observation apparatus for detecting mineral samples according to claim 1, wherein the control system controls the rotational motion of the stepper motor to realize a rotation of 90°, 180° and 360° or continuous rotation; and the angle of rotation of the mineral samples to be detected is directly determined by the angle of rotation of the stepper motor, and when the stepper motor is in a continuous rotation operating mode, the control system can input a specified angle to which the stepper motor rotates, and the control system can automatically save an image and input the image into a specified file.

3. The automatic observation apparatus for detecting mineral samples according to claim 1, wherein the high-definition camera is arranged in an enclosed hood.

4. The automatic observation apparatus for detecting mineral samples according to claim 1, wherein a rubber cup is provided outside the sample positioning head fixing device.

5. The automatic observation apparatus for detecting mineral samples according to claim 1, wherein the base is a rectangular metal plate, a through hole is respectively formed at four corners of the base, and the base is fixed on a desktop by passing four screws through the through holes.

6. The automatic observation apparatus for detecting mineral samples according to claim 1, wherein a first lug, a second lug and a third lug are provided on the base, and the supporting arm is embedded in the base; the first lug is arranged in opposite to the third lug, the second lug is arranged in opposite to the supporting arm, and a connecting line of the first lug and the third lug is vertical to a connecting line of the second lug and the supporting arm; a threaded through hole is formed on the first lug, and a first screw is mounted in the threaded through hole; a threaded through hole is formed on the second lug, and a second screw is mounted in the threaded through hole; a threaded through hole is formed on the third lug, and a third screw is mounted in the threaded through hole; a threaded through hole is formed at the lower end of the supporting arm, and a fourth screw is mounted in the threaded through hole; the first screw, the second screw, the third screw and the fourth screw are in a same plane which is parallel to the base, and the first screw, the second screw, the third screw and the fourth screw can be screwed in or out in order to fix the refractometer.

* * * * *